US010632256B2

(12) United States Patent
Sasaki (10) Patent No.: US 10,632,256 B2
(45) Date of Patent: Apr. 28, 2020

(54) DRUG SOLUTION ADMINISTRATION APPARATUS

(71) Applicant: TERUMO KABUSHIKI KAISHA, Tokyo (JP)

(72) Inventor: Shohei Sasaki, Chigasaki (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 269 days.

(21) Appl. No.: 15/587,084

(22) Filed: May 4, 2017

(65) Prior Publication Data

US 2017/0232192 A1  Aug. 17, 2017

Related U.S. Application Data

(63) Continuation of application No. PCT/JP2015/073736, filed on Aug. 24, 2015.

(30) Foreign Application Priority Data

Nov. 11, 2014  (JP) .................................. 2014-229168

(51) Int. Cl.
*A61M 5/172* (2006.01)
*A61M 5/14* (2006.01)
*A61M 5/142* (2006.01)

(52) U.S. Cl.
CPC .............. *A61M 5/172* (2013.01); *A61M 5/14* (2013.01); *A61M 5/14248* (2013.01);
(Continued)

(58) Field of Classification Search
CPC .............. A61M 5/14248; A61M 5/172; A61M 2005/14268; A61M 5/3146; A61M 2005/1402; A61M 2005/1403
See application file for complete search history.

(56) References Cited

U.S. PATENT DOCUMENTS 5,496,273 A     3/1996 Pastrone et al.
2007/0224055 A1*  9/2007 Anex ................. A61M 5/14526
                                                  417/404
(Continued)

FOREIGN PATENT DOCUMENTS

CN    101522235 A    9/2009
CN    101808680 A    8/2010
(Continued)

OTHER PUBLICATIONS

International Search Report issued in International Patent Application No. PCT/JP2015/073736 dated Dec. 22, 2015.
(Continued)

*Primary Examiner* — Lauren P Farrar
*Assistant Examiner* — James D Ponton
(74) *Attorney, Agent, or Firm* — Foley & Lardner LLP (57) ABSTRACT

A drug solution administration apparatus includes an injection unit comprising an injection member configured to inject a drug solution; a delivery unit configured to be coupled to and decoupled from the injection unit, the delivery unit comprising: a delivery member configured to deliver the drug solution to the injection member, and a delivery device configured to deliver the drug solution to the delivery member; a detection unit configured to detect whether the injection unit and the delivery unit are coupled or decoupled; and a control unit configured to control operation of the delivery device. The control unit is configured to perform at least one of (i) restricting the filling operation when the detection unit detects that the injection unit and the delivery unit are coupled, or (ii) restricting the administration operation when the detection unit detects that the injection unit and the delivery unit are decoupled.

10 Claims, 5 Drawing Sheets

(52) U.S. Cl.
CPC ... *A61M 5/1413* (2013.01); *A61M 2005/1402* (2013.01); *A61M 2005/1403* (2013.01); *A61M 2005/14268* (2013.01); *A61M 2205/121* (2013.01); *A61M 2205/14* (2013.01); *A61M 2205/3317* (2013.01); *A61M 2205/502* (2013.01); *A61M 2205/6018* (2013.01); *A61M 2205/6054* (2013.01); *A61M 2205/8206* (2013.01)

(56) References Cited

U.S. PATENT DOCUMENTS

| | | | | |
|---|---|---|---|---|
| 2010/0022988 A1* | 1/2010 | Wochner | ............ | A61M 5/14244 604/506 |
| 2011/0213306 A1* | 9/2011 | Hanson | ............... | A61M 5/1413 604/151 |
| 2012/0184907 A1* | 7/2012 | Smith | ............... | A61M 5/14248 604/152 |
| 2014/0261705 A1 | 9/2014 | Miyazaki | | |

FOREIGN PATENT DOCUMENTS

| | | |
|---|---|---|
| JP | S63-177864 A | 7/1988 |
| JP | 2004-505732 A | 2/2004 |
| JP | 2007-509661 A | 4/2007 |
| JP | 2009-016635 A | 1/2009 |
| JP | 2010-501283 A | 1/2010 |
| JP | 2010-535057 A | 11/2010 |
| JP | 2014-176454 A | 9/2014 |
| WO | WO-2005/039673 A2 | 5/2005 |
| WO | WO 2008/024814 A2 * | 2/2008 ............ A61M 5/142 |
| WO | WO-2008/024814 A2 | 2/2008 |

OTHER PUBLICATIONS

Extended European Search Report dated Jun. 6, 2018 in corresponding application No. 15858458.1.
Chinese Office Action dated Aug. 28, 2019 for corresponding Application No. 201580054056.8 (7 pages).
Japanese Office Action dated Aug. 27, 2019, for corresponding Application No. JP2016-558901 (10 pages).
Japanese Decision of Dismissal of Amendment dated Dec. 17, 2019 for corresponding Application No. 2016-558901.
Japanese Decision of Refusal dated Dec. 17, 2019 for corresponding Application No. 2016-558901.

* cited by examiner

DRUG SOLUTION ADMINISTRATION APPARATUS

CROSS-REFERENCE TO RELATED APPLICATIONS

This application is a bypass continuation of PCT Application No. PCT/JP2015/073736, filed on Aug. 24, 2015, which claims priority to Japanese Patent Application No. 2014-229168, filed on Nov. 11, 2014. These applications are hereby incorporated by reference in their entireties.

BACKGROUND

The present disclosure relates to a drug solution administration apparatus that is used to administer a drug solution into a living body.

A mobile drug solution administration apparatus for administering a drug solution such as insulin over time while being attached to the skin of a user (patient) targeted for administration is known. The drug solution administration apparatus allows automatic and continuous administration of a preset amount of the drug solution to a patient as an administration operation and also allows addition of another amount of the drug solution at the patient's instruction at the times of meal, exercise, and the like. An appropriate amount of the drug solution is administered by such a drug solution administration apparatus to the patient to allow the drug to act with sufficient efficacy.

If the administration operation is performed with air present in a drug solution flow path in the drug solution administration apparatus, or if there is a delay between when a drug delivery mechanism of the drug solution administration apparatus is started and when drug delivery is actually started, the air may be injected in a living body, or it may become impossible to accurately determine an amount of the drug solution that has been administered into the living body. Hence, the patient typically needs to perform a filling operation before starting the administration operation. The filling operation is performed as follows: a controller is operated while the drug solution administration apparatus is not attached; a slightly larger amount of the drug solution than an amount corresponding to the internal capacity of the flow path of the drug solution administration apparatus is delivered and the drug delivery is continued; accordingly, the discharge of the drug solution from the drug solution administration apparatus to the outside is visually confirmed.

If the filling operation is performed while the drug solution administration apparatus is attached, not only is the air injected into the living body, or does an accurate amount of the drug solution that has been administered into the living body become impossible to be grasped, but also may an excessive amount of the drug solution be administered into the living body when drug delivery is continued. On the other hand, if the drug solution administration apparatus is accidentally detached from the living body during the administration operation, the drug solution intended to be administered may leak to the outside of the living body so that an insufficient amount of the drug solution is administered into the living body. In addition, it is impossible to accurately determine the amount of the drug solution that has been administered into the living body. Moreover, if the administration operation is performed while the drug solution administration apparatus is not attached, the expensive drug solution leaks to the outside, and also it is difficult to accurately determine the amount of the drug solution that has been administered into a living body.

JP 2009-016635 T discloses an apparatus that is configured such that an injection unit that injects a drug solution into a living body while being attached to the living body and a delivery unit that delivers the drug solution to the injection unit can be coupled to each other. The apparatus notifies a patient of a coupled/decoupled state of the injection unit and the delivery unit and encourages the administration of an appropriate amount of the drug solution.

SUMMARY

When using the apparatus of JP 2009-016635 T, if a patient does not notice the notification or cannot fully understand the content of the notification, the apparatus may not administer an appropriate amount of drug solution, which leads to insufficient efficacy.

Hence, an object of the present disclosure is to provide a drug solution administration apparatus that allows a user (patient) to obtain sufficient efficacy by administering an appropriate amount of drug solution into a living body.

A drug solution administration apparatus according to one embodiment includes: an injection unit including an injection member that injects a drug solution into a living body; a delivery unit configured to be able to be coupled to and decoupled from the injection unit, the delivery unit including a delivery member that delivers the drug solution to the injection member, and a delivery device that delivers the drug solution stored to the delivery member; a detection unit configured to detect coupling and decoupling of the injection unit and the delivery unit; and a control unit configured to control operation of the delivery device, wherein the control unit restricts the delivery device's operation of filling the drug solution in the delivery member or the injection member and/or operation of administering the drug solution into the living body, on the basis of a detection result of the detection unit.

In the drug solution administration apparatus described in the present disclosure, the control unit restricts the delivery device's operation of filling a drug solution in the delivery member or injection member and/or operation of administering the drug solution into a living body, on the basis of a detection result of the detection unit. Accordingly, an appropriate amount of the drug solution can be administered into the living body, and a user (patient) of the drug solution administration apparatus can obtain sufficient efficacy.

Moreover, when the detection unit has detected a coupled state of the injection unit and the delivery unit, the control unit restricts the filling operation of the delivery device. Accordingly, it is possible to prevent an excessive amount of the drug solution from being accidentally administered into the living body and also to prevent air from being injected into the living body and to accurately determine an amount of the drug solution that has been administered into the living body.

This simple configuration that restricts the filling operation of the delivery device can help to prevent drug delivery to the delivery member.

Moreover, when the detection unit has detected a decoupled state of the injection unit and the delivery unit, the control unit restricts the administration operation of the delivery device. Accordingly, it is possible to prevent an insufficient amount of the drug solution from being accidentally administered into the living body and also to prevent the expensive drug solution from leaking and to accurately determine an amount of the drug solution that has been administered into the living body.

This simple configuration that restricts the administration operation of the delivery device can help to prevent drug delivery to the injection member.

Moreover, the detection unit includes a first detected member having a contact surface and a first detection member that detects contact with the first detected member, which correspond to the injection unit and the delivery unit. This reliable and inexpensive configuration can help to ensure the detection of the coupling and decoupling of the injection unit and the delivery unit.

Moreover, the detection unit may include a second detected member that produces a magnetic field and a second detection member that detects the magnetic field of the second detected member. This simple configuration can help to ensure the detection of the coupling and decoupling of the injection unit and the delivery unit without, for example, the second detected member and the second detection member necessarily coming into contact with each other.

DETAILED DESCRIPTION

Embodiments of the invention are described hereinafter with reference to the drawings. The dimensional ratios in the drawings are exaggerated for convenience of description. They may be different from actual ratios. In FIGS. 1 to 4 and FIGS. 8A and 8B, the directions of a drug solution administration apparatus are indicated by arrows X, Y, and Z. The direction of the arrow expressed by X indicates a lateral direction X of the drug solution administration apparatus. The direction of the arrow expressed by Y indicates a longitudinal direction Y of the drug solution administration apparatus. The direction of the arrow expressed by Z indicates a thickness direction Z of the drug solution administration apparatus.

One example of the drug solution administration apparatus, an insulin pump 100, will first be described.

Firstly, the configuration of the insulin pump 100 is described with reference to FIGS. 1 to 4.

Figure 1:
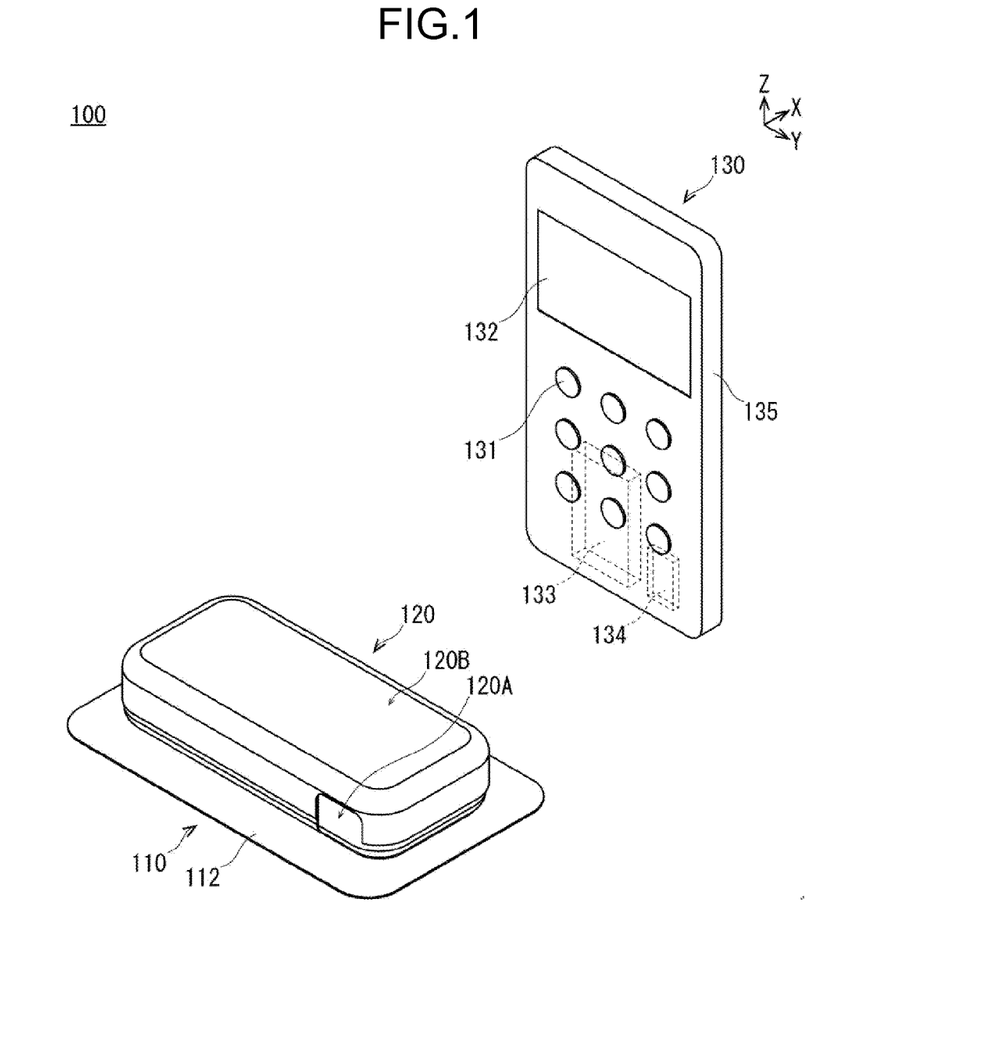
FIG. 1 is a perspective view illustrating a drug solution administration apparatus according to an embodiment.
Figure 2A:
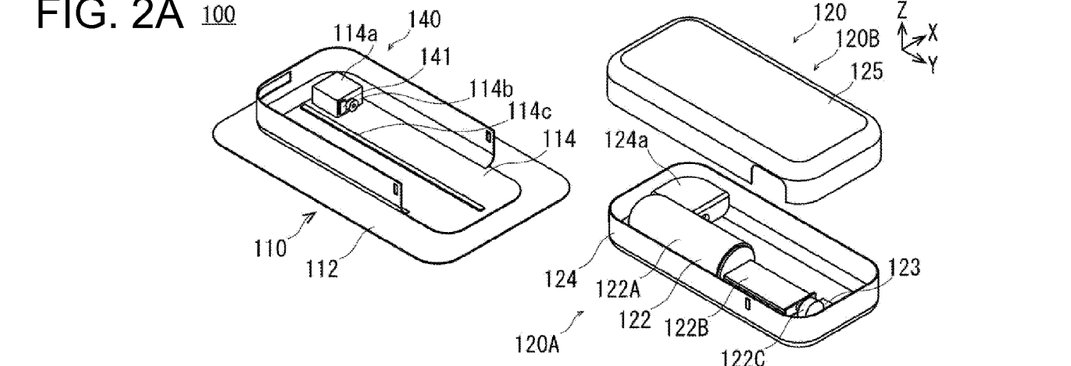
FIGS. 2A to 2C are perspective views illustrating configurations, excluding a controller, of the drug solution administration apparatus of FIG. 1 in an exploded manner.
Figure 2B:
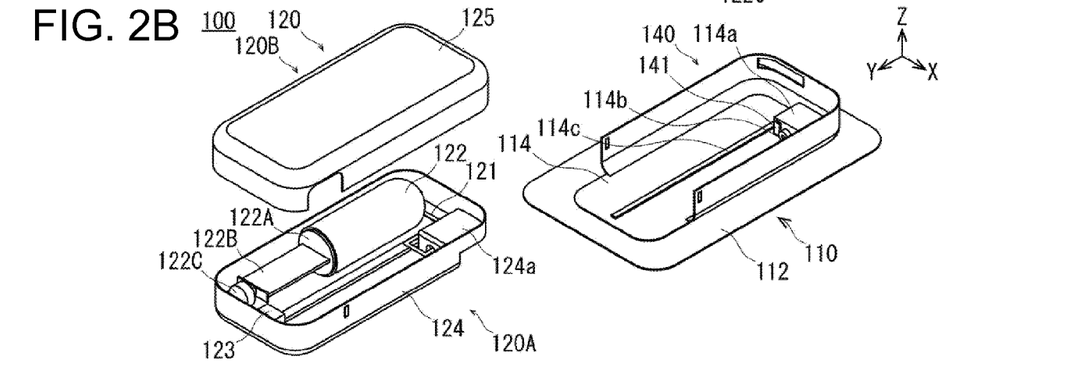
Figure 2C:
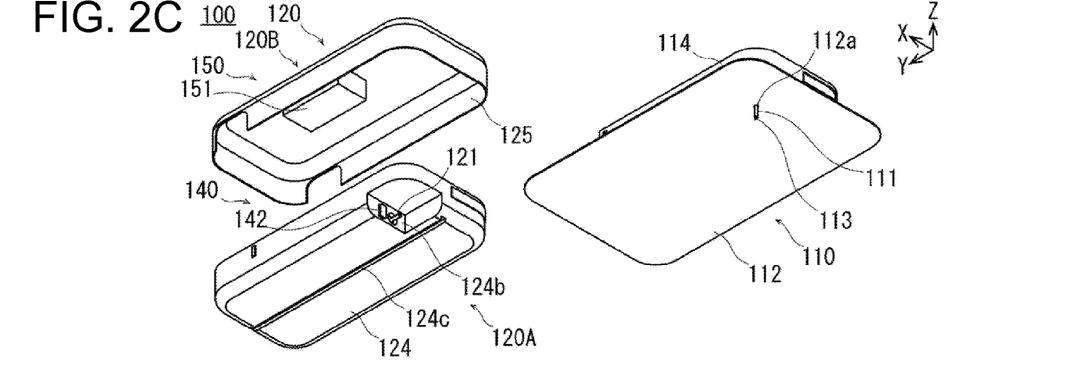
Figure 3A:
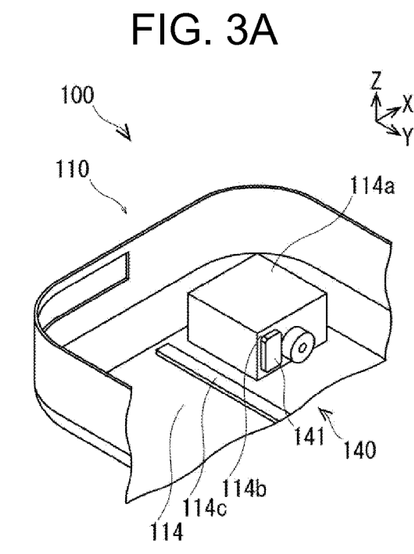
FIGS. 3A and 3B are perspective views partially illustrating an injection unit and a delivery unit, and a detection unit of the drug solution administration apparatus of FIG. 1.
Figure 3B:
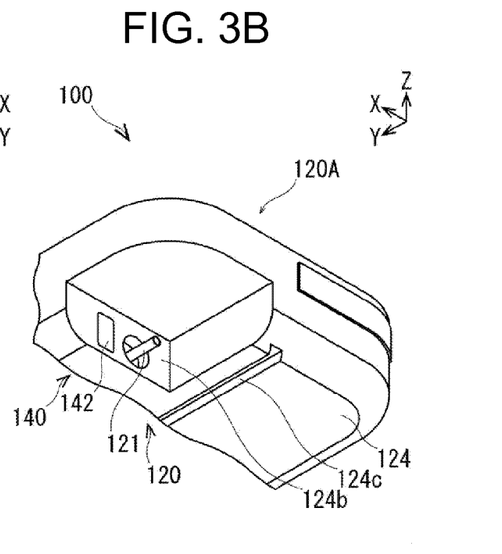
Figure 4:
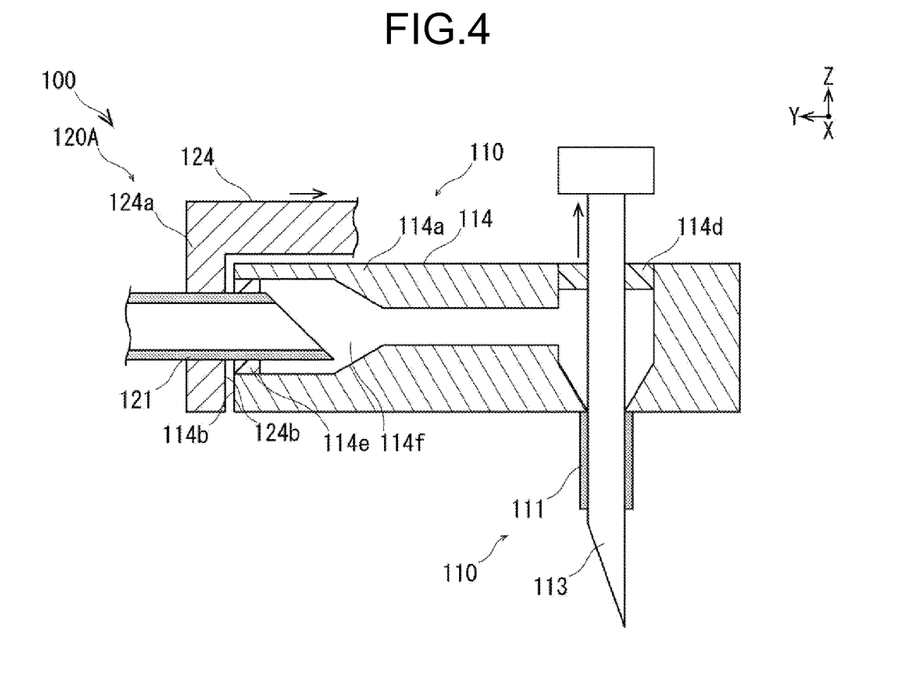
FIG. 4 is a cross-sectional view illustrating a configuration related to a flow path of a drug solution in a coupled state of the injection unit and the delivery unit of the drug solution administration apparatus of FIG. 1.

FIG. 1 is a perspective view illustrating the insulin pump 100 according to the embodiment. FIGS. 2A to 2C are exploded perspective views illustrating configurations, excluding a controller 130, of the insulin pump 100 of FIG. 1. FIG. 2A illustrates, from a top surface side, the insulin pump 100 with a disposable injection unit 110 located at the left side. FIG. 2B illustrates, from the top surface side, the insulin pump 100 with the disposable injection unit 110 located at the right side. FIG. 2C illustrates, from a bottom surface side configured to face a living body surface, the insulin pump 100 with the disposable injection unit 110 located at the right side. FIGS. 3A and 3B are perspective views illustrating portions of the disposable injection unit 110 and a disposable delivery portion 120A, and a detection unit 140 of the insulin pump 100 of FIG. 1. FIG. 3A illustrates the disposable injection unit 110 and the detection unit 140 from the top surface side. FIG. 3B illustrates the disposable delivery portion 120A and the detection unit 140 from the bottom surface side. FIG. 4 is a cross-sectional view illustrating a configuration related to a flow path of a drug solution in a coupled state of the disposable injection unit 110 and the disposable delivery portion 120A of the insulin pump 100 of FIG. 1.

The insulin pump 100 includes an injection unit (corresponding to the disposable injection unit 110), a delivery unit 120 (corresponding to the disposable delivery portion 120A and a reusable delivery portion 120B), the controller 130, the detection unit 140, and a control unit 150.

The disposable injection unit 110 injects a drug solution, such as insulin S, into a living body.

The disposable injection unit 110 includes an injection member (corresponding to a cannula 111), a cradle 112, a puncture needle 113, and a housing 114. The disposable injection unit 110 is configured so as to be disposed without being reused after completing the injection of the insulin S over several days for hygienic reasons.

The cannula 111 injects the drug solution (corresponding to the insulin S) into the living body. As illustrated in FIG. 2C, the cannula 111 is connected to the housing 114, and penetrates an introduction hole 112a of the cradle 112. The cannula 111 is made of a resin material such as polyurethane, nylon, or ethylene tetrafluoroethylene copolymer (ETFE), and is formed in a hollow cylindrical shape. As illustrated in FIG. 4, the cannula 111, together with the puncture needle 113 penetrating through the internal cavity of the cannula 111, is inserted into the living body to lie in the living body. After the puncture needle 113 is removed from the internal cavity of the cannula 111, the cannula 111 acts as a flow path for injecting the insulin S into the living body.

The cradle 112 holds the cannula 111 on the living body. In other words, the cradle 112 is affixed to the living body surface to fix the position of the cannula 111. The cradle 112 is made of a material having flexibility so as to lie along the living body surface, and is formed in a rectangular shape. One surface of the cradle 112 is coated with adhesive so as to come into intimate contact with the living body surface. The other surface of the cradle 112 is connected to the housing 114.

The puncture needle 113 is made of metal such as stainless steel, aluminum, an aluminum alloy, titanium, or a titanium alloy. As illustrated in FIG. 4, a tip of the puncture needle 113 has an acute-angled cutting edge surface so as to be inserted into the living body. After the puncture needle 113 is inserted into the living body, penetrating through the internal cavity of the cannula 111, the puncture needle 113 is removed. An enclosed state of a flow path 114f of the insulin S is maintained by a sealing member member 114d that is provided to the housing 114 and has been penetrated by the puncture needle 113. The housing 114 integrally holds the cannula 111, the cradle 112, and the puncture needle 113. The disposable delivery portion 120A is coupled to the housing 114.

As illustrated in FIG. 4, the housing 114 includes the cannula 111 and the puncture needle 113 in a coupled portion 114a that is coupled to a coupling portion 124a of the disposable delivery portion 120A described below. The coupling portion 124a of the disposable delivery portion 120A is coupled to the coupled portion 114a to cause a delivery tube 121 to penetrate the coupled portion 114a; accordingly, the flow path 114f of the insulin S is formed from the delivery tube 121 to the cannula 111. With the removal of the puncture needle 113, the sealing member 114d sealing the opening maintains the enclosed state of the flow path 114f in the coupled portion 114a. A sealing member 114e sealing an opening of the coupled portion 114a, which is created by being penetrated by the delivery tube 121, similarly maintains the enclosed state of the flow path 114f with the delivery tube 121 penetrating the coupled portion 114a.

A guide portion 114c that is coupled to a disposable portion housing 124 of the disposable delivery portion 120A is formed on an inner surface of the housing 114. The guide portion 114c includes a straight protrusion extending along the longitudinal direction Y. As illustrated in FIGS. 2A and 2B, a contact portion 114b provided on one surface of the coupled portion 114a of the housing 114 faces a contact portion 124b provided on one surface of the coupling portion 124a of the disposable portion housing 124.

The delivery unit 120 is configured including the disposable delivery portion 120A and the reusable delivery portion 120B to deliver the insulin S to the disposable injection unit 110.

The disposable delivery portion 120A and the reusable delivery portion 120B are configured so as to be able to be coupled to and decoupled from the disposable injection unit 110.

The disposable delivery portion 120A includes a delivery member (corresponding to the delivery tube 121), a delivery device 122, a battery 123, and the disposable portion housing 124. The disposable delivery portion 120A is configured so as to be disposed without being reused after completing the delivery of the insulin S over several days for hygienic reasons.

The delivery tube 121 delivers the insulin S to the cannula 111 through the flow path 114f. The delivery tube 121 is made of, for example, metal such as stainless steel, aluminum, an aluminum alloy, titanium, or a titanium alloy, or a resin material such as polyurethane, nylon, or ethylene tetrafluoroethylene copolymer (ETFE). The delivery tube 121 is formed in a tube shape including a flow path that allows the insulin S to flow therethrough. One end of the delivery tube 121 communicates with the delivery device 122. As illustrated in FIG. 4, when the disposable portion housing 124 of the disposable delivery portion 120A is coupled to the housing 114 of the disposable injection unit 110, the other end of the delivery tube 121 penetrates through the flow path 114f leading to the cannula 111. The sealing member 114e that is provided at the disposable portion housing 124 and has been penetrated by the delivery tube 121 maintains the enclosed state of the flow path 114f of the insulin S.

The delivery device 122 stores the insulin S and delivers the stored insulin S to the delivery tube 121. The delivery device 122 is configured including a syringe 122A in which the insulin S is stored, a plunger 122B that delivers the insulin S in the syringe 122A to the delivery tube 121, and a drive motor 122C that exerts pressure on the plunger 122B.

The battery 123 supplies electric power to the drive motor 122C of the delivery device 122.

The disposable portion housing 124 integrally holds the delivery tube 121, the delivery device 122, and the battery 123. The disposable portion housing 124 is coupled to the disposable injection unit 110. The disposable portion housing 124 internally introduces the delivery tube 121 into the coupling portion 124a, which is coupled to the housing 114 of the disposable injection unit 110. A guide portion 124c, which is coupled to the housing 114 of the disposable injection unit 110, is formed on an outer surface of the disposable portion housing 124. The guide portion 124c is formed so as to be a straight groove along the longitudinal direction Y.

The reusable delivery portion 120B includes a reusable portion housing 125. The reusable delivery portion 120B is reused at the time of the next delivery of the insulin S after completing the delivery of the insulin S over several days. The reusable portion housing 125 is detachably connected to the disposable portion housing 124 so as to protect the constituent members of the disposable delivery portion 120A. A control circuit 151 of the control unit 150, which controls the operation of the delivery device 122, is mounted on an inner surface of the reusable portion housing 125. The reusable portion housing 125 includes an unillustrated contact that is electrically connected to the battery 123 when connected to the disposable portion housing 124. Power is supplied to the control unit 150 via the contact.

It is also possible to have a configuration where the drive motor 122C is placed in the reusable delivery portion 120B, the configuration including a mechanism where a gear or the like converts the rotation of the drive motor 122C into the pressing force of the plunger 122B of the disposable delivery portion 120A when the disposable delivery portion 120A and the reusable delivery portion 120B are connected.

The controller 130 allows the user (patient) to instruct the delivery unit 120 to perform the filling operation, the administration operation, and the like of the insulin S. The controller 130 includes an input button 131, a monitor 132, a control circuit 133, a battery 134, and a housing 135.

The input button 131 transmits, to the control circuit 133, the user (patient)'s instructions for the turning-on and -off of the power to the insulin pump 100, the filling operation, the administration operation, and the like of the insulin S, and the like.

The monitor 132 displays thereon the content of the user (patient)'s instruction via the input button 131, and the operating state of the insulin pump 100.

The control circuit 133 includes an integrated circuit. The control circuit 133 includes a microcomputer and a wireless communication device. The microcomputer is provided with a ROM where a control program to instruct the control circuit 151 for the operation of the insulin pump 100 is stored, a CPU that controls on the basis of the control program, and a RAM where the content of an instruction is temporarily stored. The wireless communication device is used to transmit and receive information between the controller 130 and the detection unit 140.

The battery 134 supplies driving power to the control circuit 133 and the monitor 132. The input button 131 and the monitor 132 are located on a surface of the housing 135. The control circuit 133 and the battery 134 are housed in the housing 135.

The detection unit 140 detects the coupling and decoupling of the disposable injection unit 110 and the disposable delivery port ion 120A.

The detection unit 140 includes a first detected member (corresponding to a contact member 141) and a first detection member (corresponding to a switch 142).

The contact member 141 is located at the contact portion 114b provided on the surface of the coupled portion 114a of the housing 114 of the disposable injection unit 110. The contact member 141 protrudes in the longitudinal direction, and includes a contact surface at its distal end. The switch 142 detects the contact of the contact member 141.

The switch 142 is located at the coupling portion 124a of the disposable delivery portion 120A. More specifically, the switch 142 is located at the contact portion 124b provided on the surface of the coupling portion 124a. The switch 142 faces the contact member 141 along the longitudinal direction. The switch 142 is connected to an unillustrated circuit including a resistive element of a predetermined resistance value, which receives the supply of power from the battery 123.

The detection unit 140 detects the value of a voltage applied to the resistive element to detect the turning-on/off of the switch. When the disposable injection unit 110 and the reusable delivery portion 120B are coupled, the switch 142 that has been pressed by the contact member 141 is turned on. In addition, the value of the voltage that is being applied to the resistive element is detected.

On the other hand, when the disposable injection unit 110 and the reusable delivery portion 120B are decoupled, the switch 142 that has moved away from the contact member 141 is turned off. In addition, the voltage across the resistive element is not detected. The switch 142 may be provided to the reusable delivery portion 120B. The contact member 141 may be provided to the disposable delivery portion 120A or the reusable delivery portion 120B, and the switch 142 may be provided to the disposable injection unit 110.

The detection unit 140 may include a piezoelectric element that converts the pressing force into an electrical signal and a photocoupler configured as a combination of a light emitting element and a light receiving element.

The control unit 150 controls the insulin pump 100.

Specifically, the control unit 150 controls the filling operation and/or administration operation of the delivery device 122.

The control unit 150 includes the control circuit 151. The control circuit 151 includes an integrated circuit, and is mounted on an inner surface of the reusable delivery portion 120B. The control circuit 151 includes a microcomputer and a wireless communication device.

The microcomputer of the control circuit 151 includes a ROM where a control program to control, for example, the drug delivery of the delivery device 122 is stored, a CPU that controls the delivery device 122 and the like on the basis of the control program, and a RAM where the driving amount of the delivery device 122 is temporarily stored. The wireless communication device is used to transmit and receive information between the controller 130 and the detection unit 140.

Next, the filling and administration operations of the insulin pump 100 are described with reference to FIGS. 5 to 7.

Figure 5:
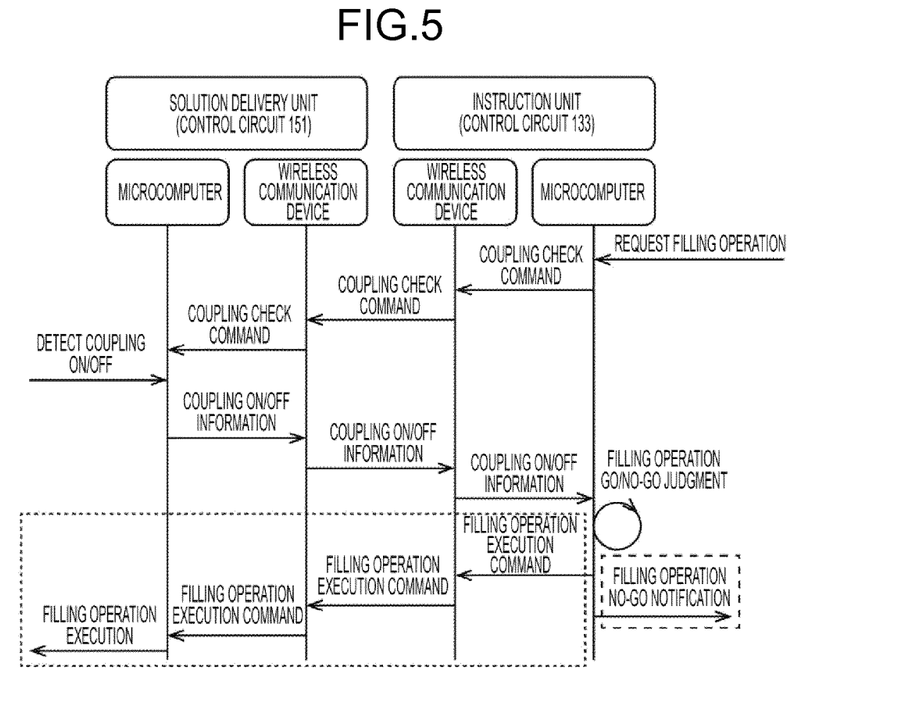
FIG. 5 is a diagram illustrating the flow of a filling operation upon the injection unit and the delivery unit being coupled or decoupled, the filling operation being related to control of the drug solution administration apparatus of FIG. 1.

FIG. 5 is a diagram illustrating the flow of the filling operation upon the disposable injection unit 110 and the delivery unit 120 being coupled or decoupled, the filling operation being related to the control of the insulin pump 100 of FIG. 1. FIG. 6 is a schematic diagram illustrating the filling operation of the insulin pump 100 under the control illustrated in FIG. 5. FIG. 7 is a diagram illustrating the flow of the administration operation upon the disposable injection unit 110 and the delivery unit 120 being decoupled, the administration operation being related to the control of the insulin pump 100 of FIG. 1.

Firstly, the filling operation of the insulin pump 100 is described.

When the detection unit 140 has detected a coupled state of the disposable injection unit 110 and the disposable delivery portion 120A, the control circuit 133 of the controller 130 restricts the filling operation of the delivery device 122. In other words, the delivery device 122 restricts drug delivery to the delivery tube 121 in the filling operation.

Such control can prevent a user (patient) of the insulin pump 100 from becoming low blood sugar due to an excessive dosage of the insulin S. Moreover, it becomes possible to prevent air from being injected into a living body and grasp an accurate amount of the insulin S that has been administered into the living body. If restricting the filling operation of the delivery device 122, the control circuit 133 may be configured so as to provide a notification by sound, light, or the like.

Specifically, when the user (patient) operates the input button 131 via the controller 130 to perform the filling operation, such control as illustrated in FIG. 5 is executed.

With the operation on the input button 131, a request for the filling operation is made to the microcomputer of the control circuit 133. The microcomputer of the control circuit 133, which has received the filling operation request, issues a command to check the coupling state of the disposable injection unit 110 and the disposable delivery portion 120A, to the wireless communication device of the control circuit 133. Information is transmitted by Serial Peripheral Interface (SPI) communication between the wireless communication device and the microcomputer of the control circuit 133.

The wireless communication device of the control circuit 133 of the controller 130 issues a command to check the coupling state of the disposable injection unit 110 and the disposable delivery portion 120A, to the wireless communication device of the control circuit 151 mounted in the delivery unit 120 (the reusable delivery portion 120B). Information is transmitted by wireless communication between the controller 130 and the control circuit 151 of the reusable delivery portion 120B.

The wireless communication device of the control circuit 151, which has received the command to check the coupling state, causes the microcomputer of the control circuit 151 to check the coupling state of the disposable injection unit 110 and the disposable delivery portion 120A. Information is transmitted by SPI communication between the wireless communication device and the microcomputer of the control circuit 151. The microcomputer of the control circuit 151 checks, at the detection unit 140, the coupling state of the disposable injection unit 110 and the disposable delivery portion 120A (whether or not the contact member 141 and the switch 142 are in contact with each other).

The detection unit 140 transmits the coupling state of the disposable injection unit 110 and the disposable delivery portion 120A to the microcomputer of the control circuit 151. The coupling state of the disposable injection unit 110 and the disposable delivery portion 120A is transmitted sequentially from the microcomputer to the wireless communication device of the control circuit 151 to the wireless communication device of the control circuit 133 to the microcomputer of the control circuit 133.

The microcomputer of the control circuit 133 judges whether or not to allow the filling operation of the delivery device 122 on the basis of the coupling state of the disposable injection unit 110 and the disposable delivery portion 120A.

If the disposable injection unit 110 and the disposable delivery portion 120A are coupled, the microcomputer of the control circuit 133 restricts the filling operation. In this case, the microcomputer of the control circuit 133 causes the monitor 132 to display information to the effect that the disposable injection unit 110 and the disposable delivery portion 120A are in the coupled state (ON). The microcomputer of the control circuit 133 may notify the information to the effect that the disposable injection unit 110 and the disposable delivery portion 120A are in the coupled state (ON), with a buzzer built in the controller 130.

On the other hand, if the disposable injection unit 110 and the disposable delivery portion 120A are decoupled, the microcomputer of the control circuit 133 permits the filling operation. In this case, the microcomputer of the control circuit 133 transmits a filling operation execution command sequentially from the microcomputer to the wireless communication device of the control circuit 133 to the wireless communication device of the control circuit 151 to the microcomputer of the control circuit 151. The microcomputer of the control circuit 151, which has received the filling operation execution command, causes the delivery device 122 to execute the filling operation.

Figure 6:
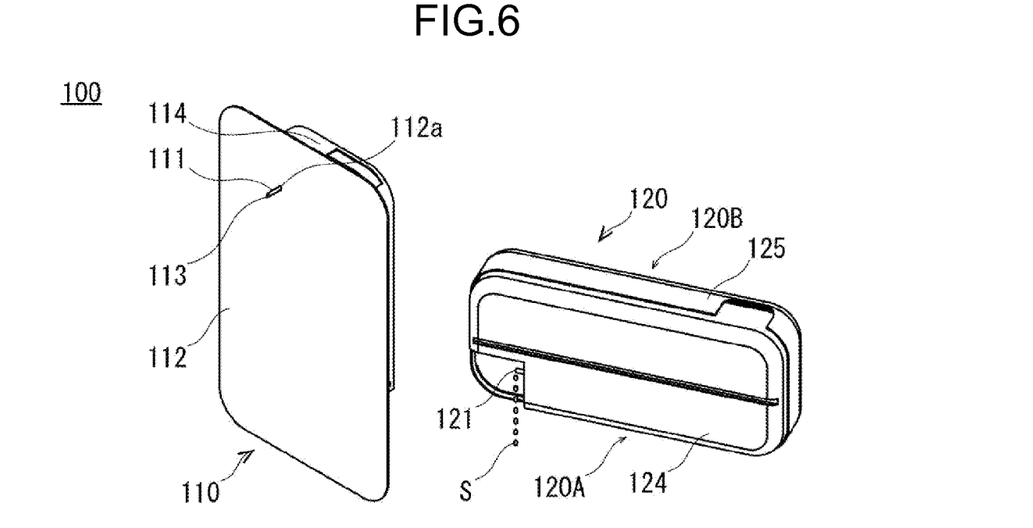
FIG. 6 is a schematic diagram illustrating the filling operation of the drug solution administration apparatus under the control illustrated in FIG. 5.

In other words, the control circuit 133 of the controller 130 instructs the delivery device 122 for the filling operation in the decoupled state of the disposable injection unit 110 and the delivery unit 120 (the disposable delivery portion 120A and the reusable delivery portion 120B) as illustrated in FIG. 6, on the basis of the detection result of the detection unit 140. In FIG. 6, part of the insulin S filled in the delivery tube 121 drops from a distal end side to the outside of the delivery tube 121. The dropped insulin S is not administered into the living body. In the embodiment, the control circuit 133 of the controller 130 restricts the filling operation of the delivery unit 120 on the basis of the detection result of the detection unit 140. However, in other embodiments, the control circuit 151 itself may restrict the filling operation of the delivery unit 120 on the basis of the detection result of the detection unit 140. If the control circuit 151 restricts the filling operation of the delivery unit, it may be informed to the controller 130 to be notified on the controller 130. Moreover, the pressing speed used in the administration operation may be very slow. Accordingly, if the filling operation is performed at this speed, it may take a long time to check the insulin S dropping from the distal end side to the outside of the delivery tube 121. Hence, the pressing speed of the plunger 122B in the filling operation may be set at a faster pressing speed than the pressing speed set in the administration operation.

Next, the administration operation of the insulin pump 100 is described.

When the detection unit 140 has detected the decoupled state of the disposable injection unit 110 and the disposable delivery portion 120A, the control circuit 151 restricts the administration operation of the delivery device 122. In other words, the delivery device 122 restricts drug delivery to the delivery tube 121 in the administration operation on the basis of the control of the control circuit 151. Such control can prevent the user (patient) of the insulin pump 100 from becoming high blood sugar due to an insufficient dosage of the insulin S. Moreover, it becomes possible to prevent the expensive insulin S from leaking to the outside and grasp an accurate amount of the insulin S that has been administered into the living body. If restricting the administration operation of the delivery device 122, the control circuit 151 may be configured so as to provide a notification by sound, light, or the like.

Figure 7:
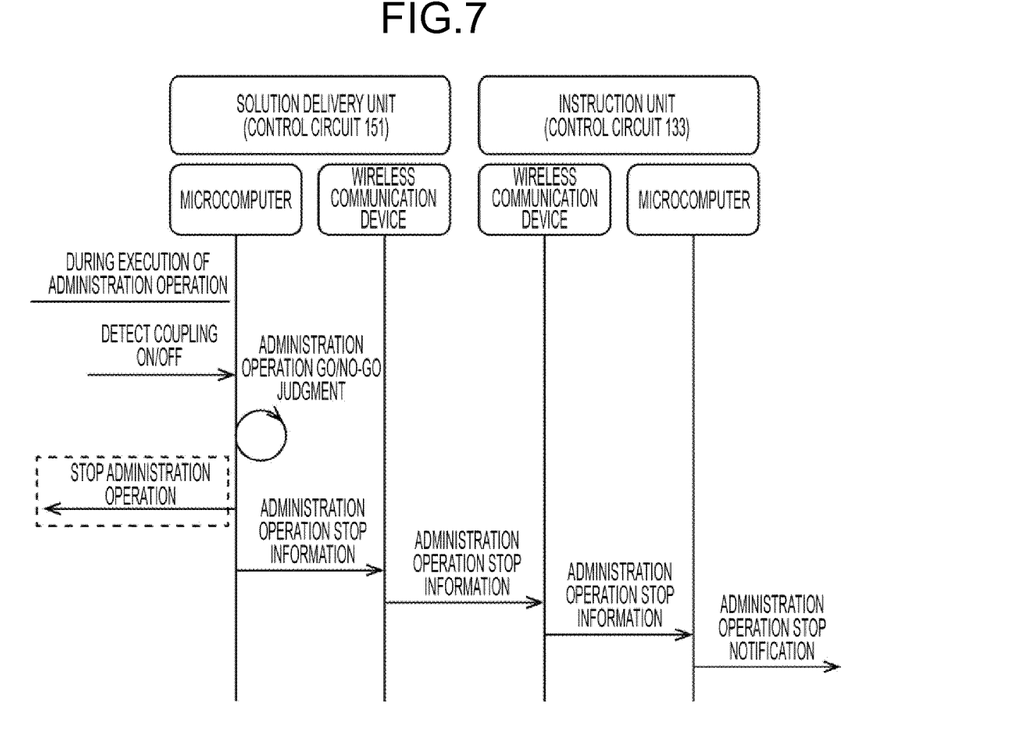
FIG. 7 is a diagram illustrating the flow of an administration operation upon the injection unit and the delivery unit being decoupled, the administration operation being related to the control of the drug solution administration apparatus of FIG. 1.

Specifically, when the disposable injection unit 110 and the disposable delivery portion 120A are decoupled during the execution of the administration operation of the delivery device 122, such control as illustrated in FIG. 7 is executed.

The microcomputer of the control circuit 151 judges whether or not to continue the administration operation of the delivery device 122 on the basis of the coupling state of the disposable injection unit 110 and the disposable delivery portion 120A. The microcomputer of the control circuit 151 makes this judgment at regular intervals on the basis of information from the detection unit 140.

If the disposable injection unit 110 and the disposable delivery portion 120A are decoupled, the microcomputer of the control circuit 151 stops the administration operation. Furthermore, information on the stoppage of the administration operation is notified sequentially from the microcomputer to the wireless communication device of the control circuit 151 to the wireless communication device of the control circuit 133 to the microcomputer of the control circuit 133. The microcomputer of the control circuit 133, which has received the information on the stoppage of the administration operation, causes the monitor 132 to display information to the effect that the disposable injection unit 110 and the disposable delivery portion 120A are in the decoupled state (OFF).

The microcomputer of the control circuit 133 may notify the information to the effect that the disposable injection unit 110 and the disposable delivery portion 120A are in the decoupled state (OFF), with the buzzer built in the controller 130.

As described above, in the insulin pump 100 according to this embodiment, the control unit 150 restricts the delivery device 122's operation of filling the insulin S in the delivery tube 121 or the cannula 111 and/or operation of administering the insulin S into a living body, on the basis of a detection result of the detection unit 140. Accordingly, an appropriate amount of the drug solution can be introduced into the living body, and the user (patient) can obtain sufficient efficacy. Specifically, the user (patient) of the insulin pump 100 can maintain an appropriate blood sugar level.

Furthermore, when the detection unit 140 has detected the coupled state of the disposable injection unit 110 and the delivery unit 120, the control unit 150 restricts the filling operation of the delivery device 122. Accordingly, an excessive amount of the insulin S can be prevented from being accidentally administered into a living body, and it becomes possible to prevent air from being injected into the living body and accurately determine an amount of the drug solution that has been administered into the living body.

The simple configuration where the control unit 150 restricts the filling operation of the delivery device 122 can help to prevent drug delivery to the delivery tube 121.

Furthermore, when the detection unit 140 has detected the decoupled state of the disposable injection unit 110 and the delivery unit 120, the control unit 150 restricts the administration operation of the delivery device 122. Accordingly, an insufficient amount of the insulin S can be prevented from being accidentally administered into the living body, and it becomes possible to prevent the expensive insulin S from leaking and grasp an accurate amount of the drug solution that has been administered into the living body.

The simple configuration where the control unit 150 restricts the administration operation of the delivery device 122 helps to prevent drug delivery to the cannula 111.

Furthermore, the detection unit 140 includes the contact member 141 having the contact surface, and the switch 142 that detects contact with the contact member 141, which correspond to the disposable injection unit 110 and the delivery unit 120. Accordingly, the very reliable and inexpensive configuration ensures the detection of the coupling and decoupling of the disposable injection unit 110 and the delivery unit 120.

<Modification>

Figure 8A:
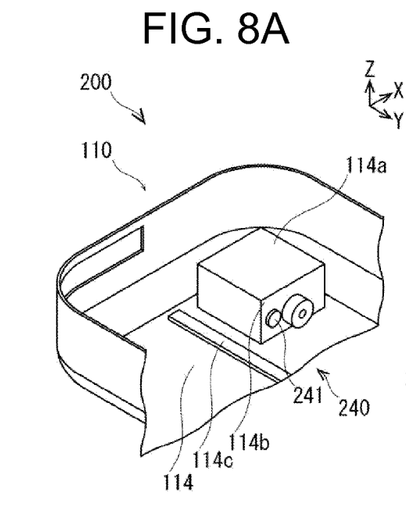
FIGS. 8A and 8B are perspective views partially illustrating an injection unit and a delivery unit, and a detection unit of a drug solution administration apparatus according to a modification of the embodiment.
Figure 8B:
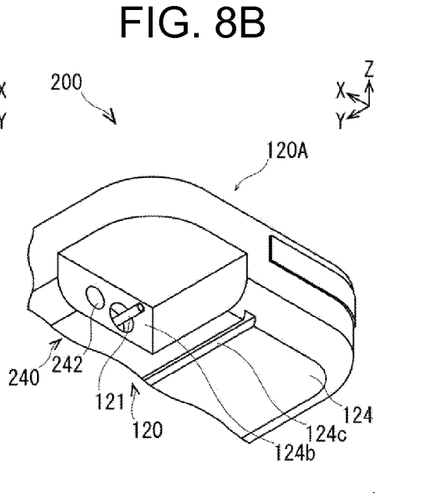

A drug solution administration apparatus (an insulin pump 200) of a modification is described.

The insulin pump 200 is different from the insulin pump 100 according to the above-mentioned embodiment in the respect that a detection unit 240 is configured to be of a magnetic detection type. In the modification of the embodiment, the same reference numerals are assigned to those having similar configurations to the above-mentioned embodiment. Overlapping descriptions are omitted.

The configuration of the insulin pump 200 is described with reference to FIGS. 8A and 8B.

FIGS. 8A and 8B are perspective views partially illustrating the disposable injection unit 110 and the disposable delivery portion 120A, and the detection unit 240 of the insulin pump 200. FIG. 8A illustrates the disposable injection unit 110 and the detection unit 240 from a top surface side. FIG. 8B illustrates the disposable delivery portion 120A and the detection unit 240 from a bottom surface side.

The detection unit 240 includes a second detected member (corresponding to a magnet 241) and a second detection member (corresponding to a magnetic sensor 242). The magnet 241 produces a magnetic field. The magnet 241 is provided to the coupled portion 114a of the housing 114 of the disposable injection unit 110. The magnetic sensor 242 detects the magnetic field of the magnet 241. The magnetic sensor 242 is provided to the coupling portion 124a of the disposable delivery portion 120A. The magnetic sensor 242 faces the magnet 241 along the longitudinal direction. If the disposable injection unit 110 and the disposable delivery portion 120A are coupled to bring the magnet 241 and the magnetic sensor 242 into contact with each other, the magnetic sensor 242 detects the magnetic field of the magnet 241.

As described above, in the insulin pump 200 according to the modification of the embodiment, the detection unit 240 includes the magnet 241 that produces a magnetic field and the magnetic sensor 242 that detects the magnetic field of the magnet 241, which correspond to the disposable injection unit 110 and the delivery unit 120. Accordingly, the very simple configuration ensures the detection of the coupling and decoupling of the disposable injection unit 110 and the delivery unit 120 without, for example, the magnet 241 and the magnetic sensor 242 necessarily coming into contact with each other.

While the drug solution administration apparatus according to the present invention has been described through the above-described embodiments and the modifications, other embodiments and modifications are possible.

For example, the drug solution administration apparatus is not limited to the embodiment in which the insulin S is injected into a living body. Rather, other drug solutions such as painkillers or anesthesia drugs may be administered into the living body using the drug solution administration apparatus.

REFERENCE NUMERAL LIST 100, 200 Insulin pump (drug solution administration apparatus)
110 Disposable injection unit (injection unit)
111 Cannula (injection member)
112 Cradle
112a Introduction hole
113 Puncture needle
114 Housing
114a Coupled portion
114b Contact portion
114c Guide portion
114d, 114e sealing member
114f Flow path
120 Delivery unit
120A Disposable delivery portion (delivery unit)
120B Reusable delivery portion (delivery unit)
121 Delivery tube (delivery member)
122 Delivery device
122A Syringe
122B Plunger
122C Drive motor
123 Battery
124 Disposable portion housing
124a Coupling portion
124b Contact portion
124c Guide portion
125 Reusable portion housing
130 Controller
131 Input button
132 Monitor
133 Control circuit
134 Battery
135 Housing
140, 240 Detection unit
141 Contact member (first detected member)
142 Switch (first detection member)
241 Magnet (second detected member)
242 Magnetic sensor (second detection member)
150 Control unit
151 Control circuit
S Insulin
X Lateral direction of the insulin pump
Y Longitudinal direction of the insulin pump
Z Thickness direction of the insulin pump

The invention claimed is:

1. A drug solution administration apparatus comprising:
an injection unit comprising an injection member configured to inject a drug solution into a living body;
a delivery unit configured to be coupled to and decoupled from the injection unit, the delivery unit comprising:
a delivery member configured to deliver the drug solution to the injection member, and
a delivery device configured to store the drug solution and to deliver the drug solution to the delivery member;

a detection unit configured to detect a coupling state of the injection unit and the delivery unit, which is either a coupled state in which the injection unit and the delivery unit are coupled, or a decoupled state in which the injection unit and the delivery unit are decoupled;

a control unit configured to control operation of the delivery device; and a controller configured to receive an input from a user and to operate the control unit;

wherein the drug solution administration apparatus is configured to perform (i) a filling operation in which the drug solution is delivered from the delivery device to the delivery member, and (ii) an administration operation in which the drug solution is administered into the living body; and wherein the controller is configured such that, upon receiving an input from the user to perform the filling operation:

the controller requests, from the control unit, the coupling state detected by the detection unit, upon determining that the injection unit and the delivery unit are in the decoupled state, the controller transmits a filling operation execution command to the control unit, and upon determining that the injection unit and the delivery unit are in the coupled state, the controller does not transmit the filling operation execution command to the control unit.

2. The drug solution administration apparatus according to claim 1, wherein the control unit is configured to restrict the administration operation when the detection unit detects that the injection unit and the delivery unit are decoupled.

3. The drug solution administration apparatus according to claim 2, wherein the control unit is configured to restrict the administration operation by restricting the delivery member from delivering the drug solution to the injection member.

4. The drug solution administration apparatus according to claim 1, wherein the detection unit comprises:

a contact surface located at the injection unit, and a detection member located at the delivery unit and configured to detect contact with the contact surface.

5. The drug solution administration apparatus according to claim 4, wherein the detection member is a switch.

6. The drug solution administration apparatus according to claim 1, wherein the detection unit comprises:

a magnetic member located at the injection unit and producing a magnetic field, and a magnetic sensor located at the delivery unit and configured to detect the magnetic field of the magnetic member.

7. The drug solution administration apparatus according to claim 1, wherein the injection member comprises a cannula.

8. The drug solution administration apparatus according to claim 7, wherein the delivery member comprises a tube.

9. The drug solution administration apparatus according to claim 8, wherein the delivery device comprises a syringe configured to store the drug solution, a plunger configured to deliver the drug solution from the syringe to the tube of the delivery member, and a drive motor configured to exert pressure on the plunger.

10. A method for controlling a drug solution administration apparatus, the method comprising:

providing the drug solution administration apparatus, which comprises:

an injection unit comprising an injection member configured to inject a drug solution into a living body;

a delivery unit configured to be coupled to and decoupled from the injection unit, the delivery unit comprising:

a delivery member configured to deliver the drug solution to the injection member, and a delivery device configured to store the drug solution and to deliver the drug solution to the delivery member;

a detection unit configured to detect a coupling state of the injection unit and the delivery unit, which is either a coupled state in which the injection unit and the delivery unit are coupled, or a decoupled state in which the injection unit and the delivery unit are decoupled;

a control unit configured to control operation of the delivery device; and a controller configured to receive an input from a user and to operate the control unit;

wherein the drug solution administration apparatus is configured to perform (i) a filling operation in which the drug solution is delivered from the delivery device to the delivery member, and (ii) an administration operation in which the drug solution is administered into the living body;

upon receiving, at the controller, an input from the user to perform the filling operation:

requesting, at the controller, from the control unit, the coupling state detected by the detection unit, upon determining that the injection unit and the delivery unit are in the decoupled state, transmitting, from the controller, a filling operation execution command to the control unit, and upon determining that the injection unit and the delivery unit are in the coupled state, not transmitting, from the controller, the filling operation execution command to the control unit.

* * * * *